United States Patent [19]

Natori

[11] Patent Number: 5,118,789
[45] Date of Patent: Jun. 2, 1992

[54] ANTIBACTERIAL POLYPEPTIDE FROM SARCOPHAGA PEREGRINA

[75] Inventor: Shunji Natori, Kita, Japan

[73] Assignee: Sanwa Kagaku Kenkyusho Co. Ltd., Nagoya, Japan

[21] Appl. No.: 711,417

[22] Filed: Jun. 5, 1991

Related U.S. Application Data

[63] Continuation-in-part of Ser. No. 173,483, Mar. 25, 1988, abandoned.

[30] Foreign Application Priority Data

Mar. 30, 1987 [JP] Japan .................. 62-77154

[51] Int. Cl.⁵ ............... A61K 37/02; A61K 37/00
[52] U.S. Cl. ................. 530/300; 530/417; 530/858
[58] Field of Search ............ 530/300, 417, 858; 514/21

[56] References Cited

FOREIGN PATENT DOCUMENTS 59-13730A 1/1984 Japan .
5913730 10/1984 Japan .
61-122299A 6/1986 Japan .
61122299 10/1986 Japan .

OTHER PUBLICATIONS

Euro. J. Biochem., vol. 106, pp. 7–16 (1980).
Okada et al, "Purification and characterization of an antibacterial protein from hemolycin of Sarcophaga peregrina (flesh fly/larvae", Chemical Abstracts, vol. 99, p. 256, ref. # 18367d, 1983.
Baba et al, "Purification of sarcotoxin III, a new antibacterial protein of S-peregrina." Chemical Abstracts, vol. 107, p. 197. Ref. # 110764n, 1987 Euro. J. Biochem., vol. 106, pp. 7–16 (1980).
Okuda et al, Biochem J., vol. 211, pp. 727–734, 1983.
Baba et al, J. Biochem., vol. 102, No. 1, pp. 69–74, 1987.
Ando et al, J. Biochem., vol. 103, No. 4, pp. 735–739, 1988.
Ando et al, Biochemistry, vol. 26, pp. 226–230, 1987.
Okada et al, The Journal of Biological Chemistry, vol., 260, No. 12, pp. 7174–7177, Jun. 25, 1985.

Primary Examiner—Ronald W. Griffin
Assistant Examiner—Abdel A. Mohamed
Attorney, Agent, or Firm—Nikaido, Marmelstein, Murray & Oram

[57] ABSTRACT

An antibacterial polypeptide is disclosed, which is immunologically produced by *Sarcophaga peregrina*, when the insect is injured in its body wall. The polypeptide has a molecular weight of about 7000.

2 Claims, 5 Drawing Sheets

C-III : Fraction area showing antibacterial activity o———o : Known polypeptide (MW; about 4000)
▲———▲ : Fractions of Peak A
●———● : Fractions of Peak B
■———■ : Fractions of Peak C
(Novel polypeptide, MW: about 7000)

Lane 1 : Known polypeptide (MW ; about 4000)
Lane 2 : Novel polypeptide (MW ; about 7000)

ANTIBACTERIAL POLYPEPTIDE FROM SARCOPHAGA PEREGRINA

This application is a continuation-in-part of application Ser. No. 173,483 filed Mar. 25, 1988, now abandoned.

BACKGROUND OF THE INVENTION

1. Field of the Invention

The present invention relates to a novel antibacterial polypeptide which is obtained from a body fluid of an insect and more particularly from flesh fly (Sarcophaga peregrina).

2. Related Arts

It has been known that a certain antibacterial substance will appear in a body fluid, when a vaccine is inoculated to an invertebrate such as insecta ["Eur. J. Biochem." Vol. 106, page 7 (1980)].

The present inventor has also found that the Sarcophaga peregrina produces a certain antibacterial polypeptide in its body fluid, when a larva of the insect is injured in its body wall. The polypeptide was isolated and purified and its physicochemical properties have been investigated [see Japanese Patent Publication Nos. 59-13730 (A) published Jan. 24, 1984 and 61-122299 (A) published Jun. 10, 1986].

Since the polypeptide induced in the insect shows a wide antibacterial spectrum and almost no toxicity, the substance has been expected to be an edible antibiotic. Its yield, however, is rather low.

SUMMARY OF THE INVENTION

A primary objective of the invention is to provide a novel antibacterial polypeptide isolated from the body fluid of the Sarcophaga peregrina larvae and which has a wide antibacterial spectrum, low toxicity and can be obtained in with higher yield than the molecules disclosed in the prior art described above.

According to the invention, the objective is accomplished by the discovery of an antibacterial polypeptide obtained from Sarcophaga peregrina injured in its body wall and having

| | |
|---|---|
| a) | a molecular weight of about 7000, as estimated (identified) by SDS polyacrylamide-gel electrophoresis, and |
| b) | an amino acid composition of |
| Asp + Asn | 12.6 (mol %) |
| Thr | 3.8 |
| Ser | 7.7 |
| Glu + Gln | 9.9 |
| Pro | 8.1 |
| Gly | 15.9 |
| Ala | 2.1 |
| Cys | 0 |
| Val | 4.6 |
| Met | 0 |
| Ile | 1.3 |
| Leu | 3.9 |
| Tyr | 5.1 |
| Phe | 5.7 |
| Lys | 6.8 |
| His | 3.1 |
| Arg | 9.3 |
| Trp | 0. |

This polypeptide shows an antibacterial activity which is comparable with that of the polypeptide (molecular weight of about 4000) disclosed in the Japanese patent publications identified above, has a relatively low toxicity and excellent thermal stability.

The polypeptide of the present invention can be obtained in a manner similar to that disclosed in said prior art, namely by rearing pupae or larvae of Sarcophaga peregrina over a certain period of time, thereafter injuring its body wall, drawing out the body fluid or homogenizing a whole body, removing solids to obtain a liquid component, and finally fractionating the liquid component by ion-exchange chromatography and HPLC reverse-phase chromatography to collect fractions with an antibacterial activity.

The reason the pupae or larvae, instead of the mature form (imago) of Sarcophaga peregrina, was selected as the producing insect is because it is known in the art that antibacterial polypeptides are also produced when an imago of the insect is injured in its body, but the specific activities of the induced polypeptides are lower in comparison with those produced by the pupa or larva thereof. The time from the insect injury to the time when the body fluid is taken out or the whole body of the insect is homogenized has been selected to give a sufficient period of time for production of the desired antibacterial polypeptide. The preferred rearing period in this instance is 24 to 48 hours. The reduction of antibacterial activity of the produced polypeptide will occur when the rearing period is too long.

The ion-exchange chromatography is carried out in a multi-step manner. In its last step, two activity peaks are eluted and collected from the CM Sepharose column. The first peak, consisting of fractions showing relatively high antibacterial activity, has been purified by HPLC reverse-phase chromatography to give an antibacterial polypeptide having a molecular weight of about 4000. This polypeptide was disclosed in Japanese Patent Publication Nos. 59-13730 (A) and 61-122299 (A). The second peak consisting of fractions showing relatively low antibacterial activity has been purified by reverse-phase HPLC in a similar manner. It has been found unexpectedly that this peak contains the antibacterial polypeptide having a molecular weight of about 7000 and amino acid composition disclosed above.

DETAILED DESCRIPTION OF THE PREFERRED EMBODIMENT

The invention will be explained further with reference to an Example for obtaining an antibacterial polypeptide, as well as Test Examples.

EXAMPLE

1) Preparation of Raw Material

A body wall of each larva of Sarcophaga peregrina (third-instar larvae, namely those matured or mellowed by repeating an ecdysis 3 times) was injured with an injection needle and then reared for 24 to 28 hours at room temperature. A tail end of the larvae was cut with scissors. The body fluid was squeezed out into ice-cooled petri dish. The body fluid was centrifuged at $200 \times g$. for 10 minutes to remove solid substances. The obtained supernatant has been employed as raw material.

For storage, the supernatant is frozen at $-80°$ C.

2) Pre-Treatments (Multi-Step Ion-Exchange Chromatography)

a) First CM cellulose column chromatography

To 30 ml of raw material, 120 ml of 10 mM-phosphate buffer was added to adjust the pH to 6.0 The resulting solution was applied onto a CM cellulose column (3.4×20.0 cm). The column was washed with 10 mM phosphate buffer, pH 6.0. Elution was done with 10 mM phosphate buffer (pH 6.0) containing 250 mM NaCl. Fractions (5 ml) were collected. Antibacterial activity was assayed according to the method of Okada et al and using an *Escherichia coli* (K12 594) strain ["Biochem. J." Vol. 211, pages 724 to 734 (1983)]. Additionally, adsorbances at 250 and 650 nm were measured to identify fraction(s) having antibacterial activity.

b) Sephadex G-50 column chromatography

The antibacterial fractions confirmed in said Item a were combined and heated at 100° C. for 10 minutes and then centrifuged to remove a precipitate formed therein. The resulting supernatant was concentrated through ultrafiltration. The concentrate was applied to a Sephadex G-50 column (1.5×60.0 cm) and eluted with 10 mM phosphate buffer (pH 6.0) containing 130 mM NaCl. Two milliliter fractions were collected. Antibacterial activity and an absorbance at 280 nm of each fraction were assayed as described in a).

The results obtained in a and b are substantially the same as those disclosed in the aforementioned Japanese Patent Publications 59-13730 (A) and 61-122299 (A).

c) Second CM cellulose column chromatography

The fractions showing highest antibacterial activity were pooled and diluted 5 times (vol/vol) with 10 mM-phosphate buffer, pH 6.0. The solution was applied again to a CM cellulose column (2.0×4.0 cm). The bound material was eluted with a linear gradient of 25 mM to 100 mM-NaCl in 10 mM phosphate buffer. Three milliliter fractions were collected. Antibacterial activity and absorbance at 280 nm of each fraction were measured as above. The resulting elution profile is shown in FIG. 1.

d) CM Sepharose column chromatography

Figure 1:
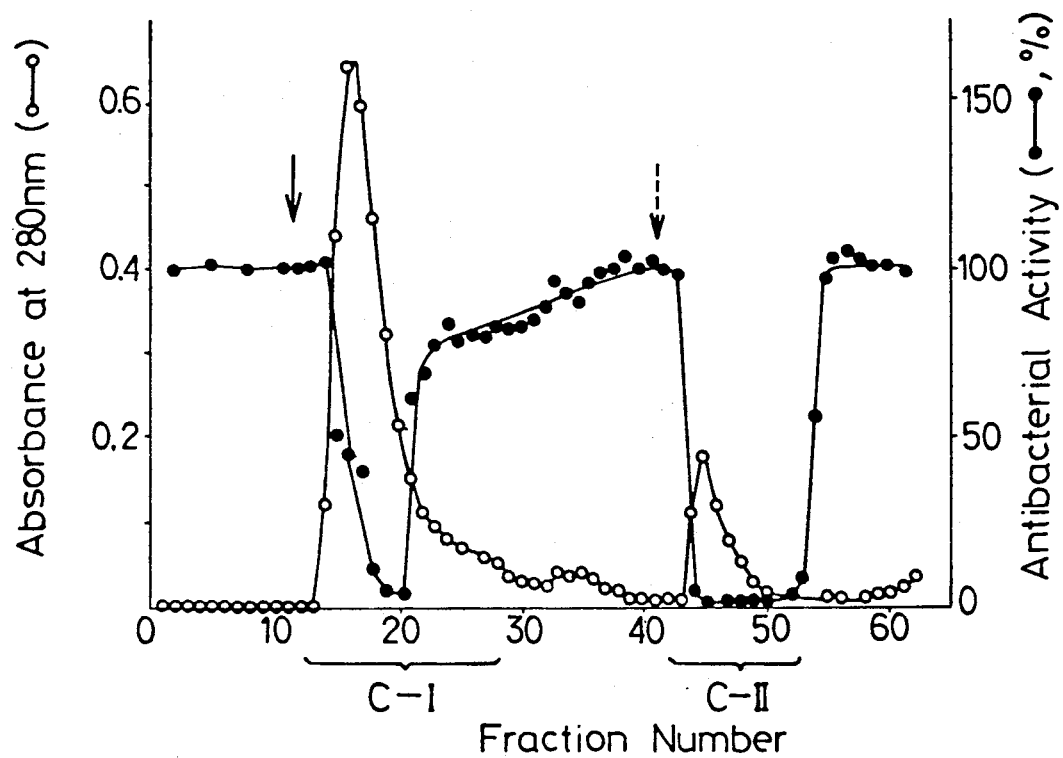
FIG. 1 shows the elution pattern of antibacterial polypeptides from a second CM cellulose column. The fractions have been eluted with a linear gradient of NaCl in phosphate buffer. The absorbance at 280 nm and an antibacterial activity of each fraction are presented.

As presented in FIG. 1, two peaks (C-I and C-II) show antibacterial activity. One of the peaks (C-I) is that obtained some time after beginning the elution with a phosphate buffer containing 130 mM-NaCl and shows relatively high antibacterial activity. If the fractions in this area are further treated and purified in a manner similar to that to be described later, an antibacterial polypeptide having a molecular weight of about 4000 can be obtained, as disclosed in the aforesaid Japanese Patent Publications 59-13730 (A) and 61-122299 (A).

Fractions 44-53 (30 ml total volume) in the C-II area are obtained some time after beginning the elution with a phosphate buffer containing 260 mM-NaCl and show relatively low antibacterial activity. The fractions were pooled and diluted with 250 ml of ammonium formate solution.

A CM Sepharose column (0.8×20 cm) was equilibrated with 10 mM ammonium formate solution and the diluted solution of pooled fractions 44-53 was applied on the column. The adsorbed proteins were eluted with 60 ml of a linear gradient of 0.1M to 0.5M-ammonium formate solution. One millimeter fractions were collected. Antibacterial activity and absorbance at 280 nm of each fraction were measured as described in a. Results are shown in FIG. 2.

3) Purifying Treatment (Purification of Antibacterial Polypeptide)

Figure 2:
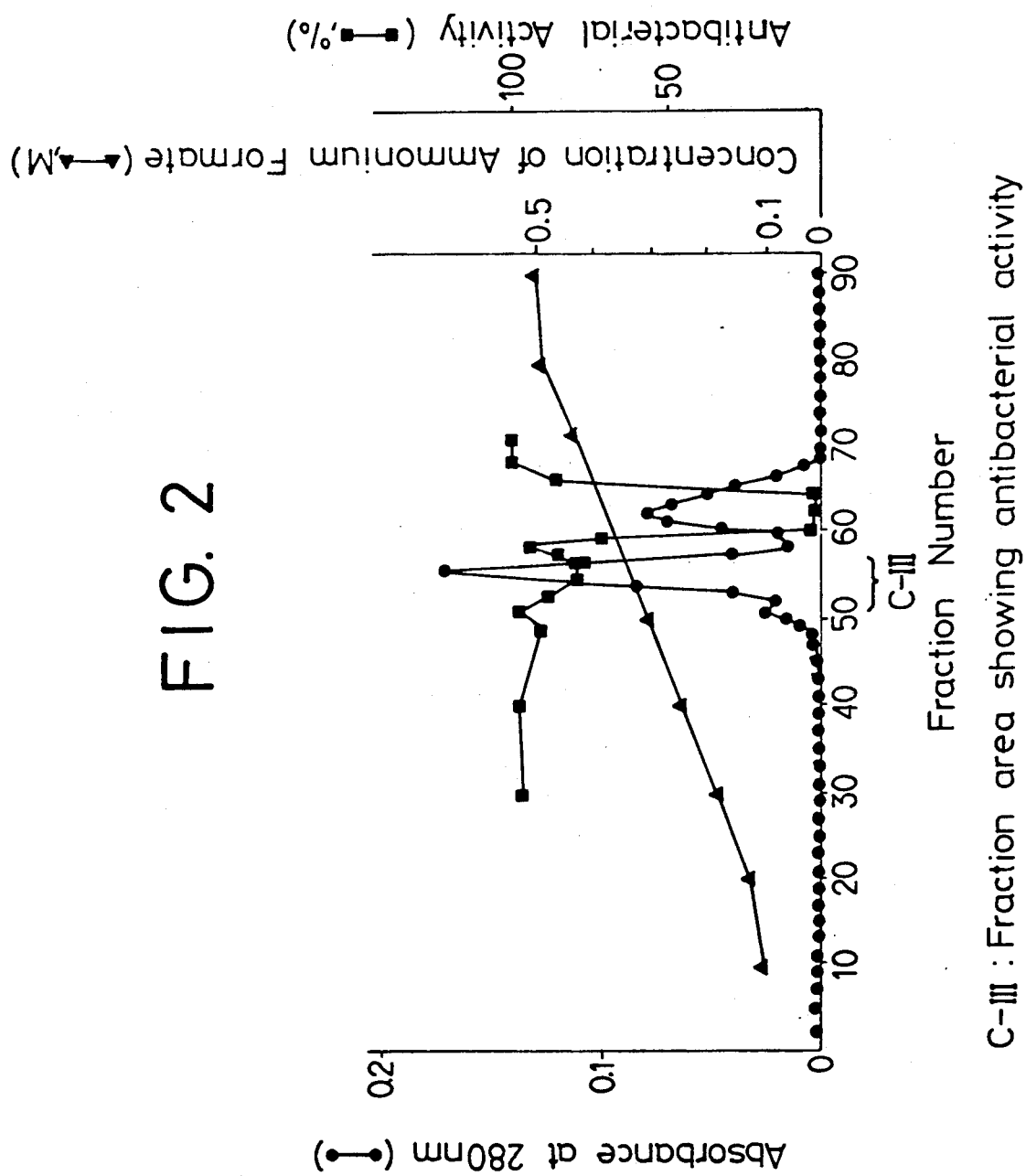
FIG. 2 is similar to FIG. 1 with the exception that it shows the relationship of the absorbance of each fraction eluted with a linear gradient of ammonium formate solution from a CM cellulose column and corresponding antibacterial activity. Peak C-II was originally loaded on the column.

As shown in FIG. 2, two fraction peaks have antibacterial activity. The first peak (C-III, Fraction Nos. 52 to 56, 5 ml in total) which shows relatively high antibacterial activity was recovered and concentrated. The concentrate was fractionated by reverse-phase HLPC (Synchropack RPP-C18 column) chromatography under following conditions.

Reagent A: 0.05% Trifluoroacetate/water,

Reagent B: 0.05% Trifluoroacetate/99% Acetonitrile,

Gradient: Linear gradient with use of 15% Reagent B in Reagent A and 50% Reagent B in Reagent A, Flow rate: 2 ml/min.

Figure 3:
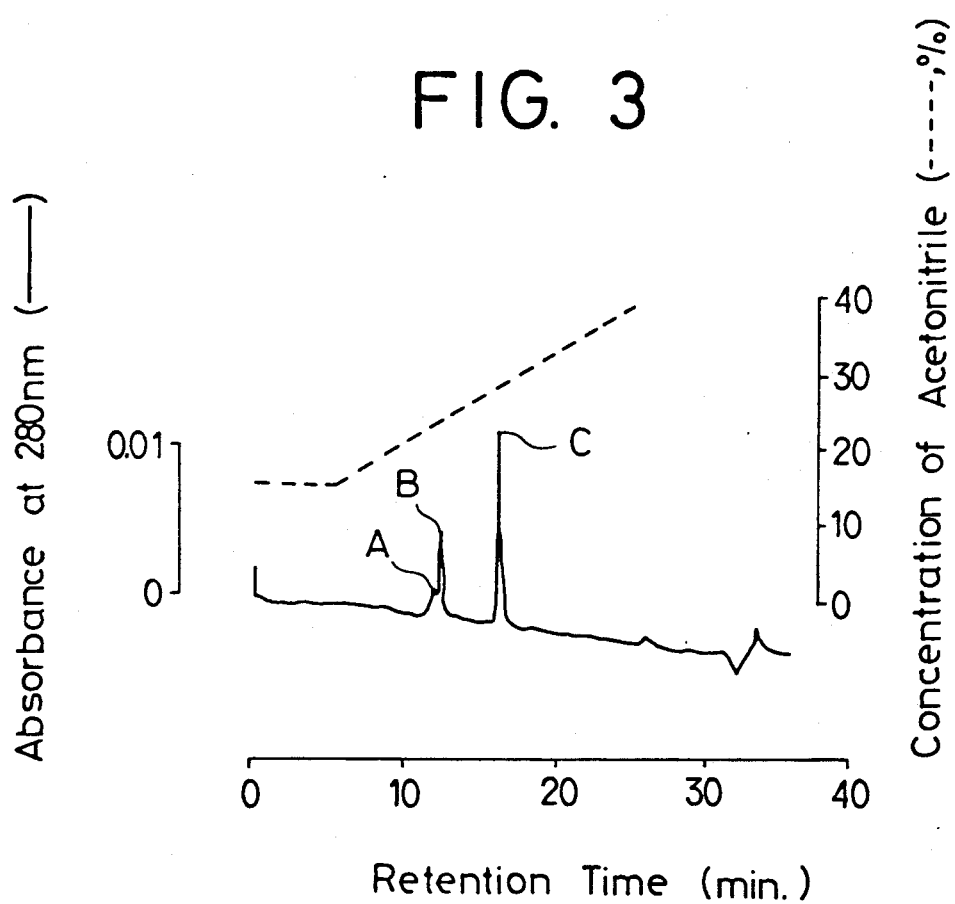
FIG. 3 shows a resolution profile of the C-III peak on reverse-phase HPLC. An acetonitrile linear gradient has been used for desorption of polypeptides from the column.

Results are shown in FIG. 3. An increase in a concentration of acetonitrile yielded fractions showing peaks (A, B and C) in absorbance.

Figure 4:
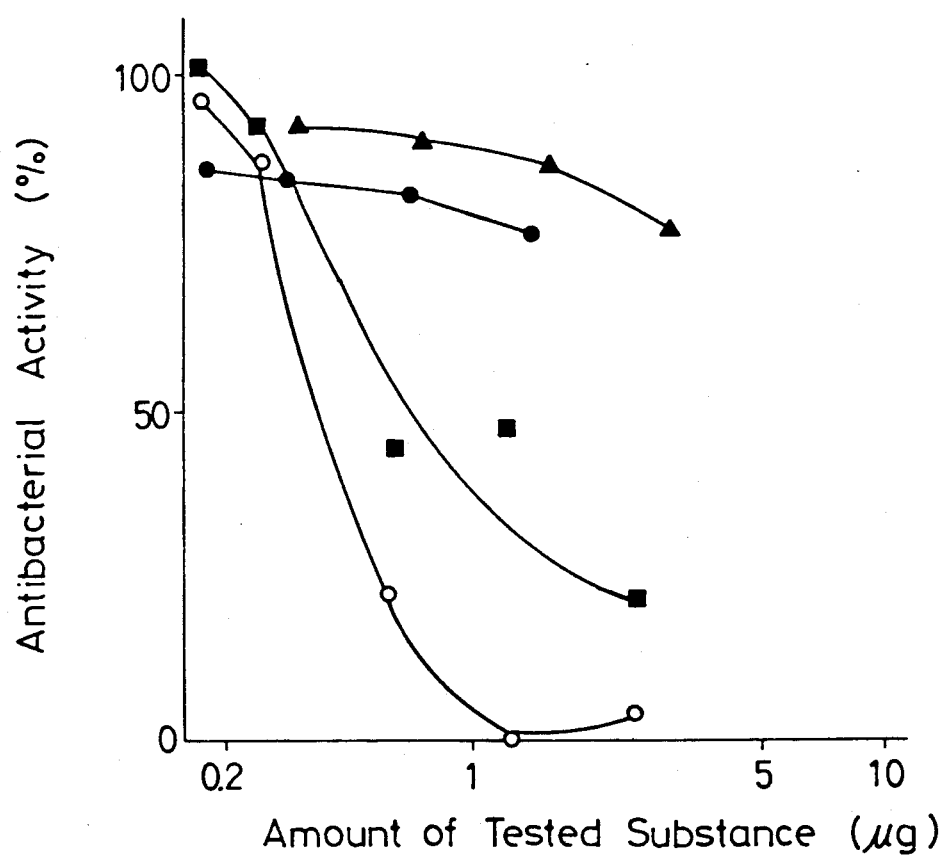
FIG. 4 is a comparison of anti-virus activities of pooled peaks A, B and C in FIG. 3 and a known antibacterial polypeptide having molecular weight of about 4000 plotted against amount of tested substance.

Each fraction area was recovered and the antibacterial activity thereof was measured as described in a. Results are shown in FIG. 4. Only the fractions corresponding to the peak C show the antibacterial activity.

In FIG. 4, there is also shown as a reference, the antibacterial activity of the known antibacterial polypeptide disclosed in Japanese Patent Publications 59-13730 (A) and 61-122299 (A) and having molecular weight of about 4000. Comparing the data thereof with those in the antibacterial polypeptide (fractions corresponding to peak C) according to the invention, the latter is somewhat weak.

TEST EXAMPLE 1

(Measurement of Molecular Weight)

A molecular weight of the antibacterial polypeptide (fractions corresponding to peak C) obtained by said Example was estimated by 15% SDS polyacrylamide-gel electrophoresis. The antibacterial polypeptide disclosed in Japanese Patent Publications 59-13730 (A) and 61-122299 (A) was used as a control. This polypeptide has molecular weight of about 4000. Before electrophoresis, all samples were pre-treated with 1% SDS and 2% β-mercaptoethanol. Chymotrypsinogen (MW: 25,000), cytochrome C (MW: 12,400) and aprotinin (MW: 6,500) were selected as molecular weight markers.

Figure 5:
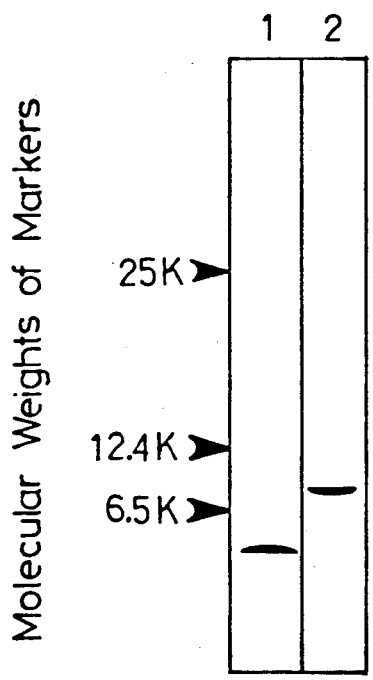
FIG. 5 shows the results of SDS polyacrylamide-gel electrophoresis of purified novel peptide M.W. 7000 and known peptide M.W. 4000. Bars at the left indicate positions of molecular weight markers run in parallel.

Results are shown in FIG. 5. From the comparison with the positions of the molecular weight markers, it is apparent that the control sample (Lane 1) and test sample (Lane 2) have molecular weight of about 4000 and about 7000, respectively. Thus both antibacterial polypeptides are different.

TEST EXAMPLE 2

(Amino Acid Analysis)

25 μg of the antibacterial polypeptide (fractions corresponding to peak C) obtained by said Example was treated with 6N-HCl for 12 hour at 120° C. to cause a hydrolysis thereof. An amino acid analysis of the resulting hydrolysate was carried out with use of an automatic amino acid analyzer (Type 835, manufactured and marketed by Hitachi Ltd., Japan). As a result, it was found that the antibacterial polypeptide has the following amino acid composition.

| | |
|---|---|
| Asp + Asn | 12.6 (mol %) |
| Thr | 3.8 |
| Ser | 7.7 |
| Glu + Gln | 9.9 |
| Pro | 8.1 |
| Gly | 15.9 |
| Ala | 2.1 |
| Cys | 0 |
| Val | 4.6 |
| Met | 0 |
| Ile | 1.3 |
| Leu | 3.9 |
| Tyr | 5.1 |
| Phe | 5.7 |
| Lys | 6.8 |
| His | 3.1 |
| Arg | 9.3 |
| Trp | 0. |

TEST EXAMPLE (Toxicity)

The antibacterial polypeptide obtained in the Example was dissolved in saline, and the resulting solution was injected subcutaneously or intra peritoneally into BALB/c mice and ICR mice over 10 days in a amount of 100 μg/kg. Neither anaphylactic shock nor necrosis, inflammation or the like, have been observed in autopsied animals.

TEST EXAMPLE (Thermal Stability)

The antibacterial polypeptide obtained in the Example was dissolved in saline, and the resulting solution was heated to 100° C. and kept for 20 minutes at that temperature, and then left to stand to allow cooling. Antibacterial activity of the solution was measured in accordance with the method proposed by Okada et al. No noticeable reduction in the activity has been found.

What is claimed is:

1. A heat-stable, antibacterial polypeptide obtained from haemolymph of a third-instar *Sarcophaga peregrina* larvae injured in its body wall and having

| | |
|---|---|
| a) a molecular weight of about 7,000 when it was measured by SDS polyacrylamide-gel electrophoresis, and | |
| b) an amino acid composition of | |
| Asp + Asn | 12.6 (mol %) |

-continued

| | |
|---|---|
| Thr | 3.8 |
| Ser | 7.7 |
| Glu + Gln | 9.9 |
| Pro | 8.1 |
| Gly | 15.9 |
| Ala | 2.1 |
| Cys | 0 |
| Val | 4.6 |
| Met | 0 |
| Ile | 1.3 |
| Leu | 3.9 |
| Tyr | 5.1 |
| Phe | 5.7 |
| Lys | 6.8 |
| His | 3.1 |
| Arg | 9.3 |
| Trp | 0.— |

2. A heat-stable, antibacterial polypeptide obtained from haemolymph of a third-instar *Sarcophaga peregrina* larvae injured in its body wall, said polypeptide having a molecular weight of about 7,000, as estimated by SDS polyacrylamide-gel electrophoresis, and an amino acid composition of:

| | |
|---|---|
| Asp + Asn | 12.6 (mol %) |
| Thr | 3.8 |
| Ser | 7.7 |
| Glu + Gln | 9.9 |
| Pro | 8.1 |
| Gly | 15.9 |
| Ala | 2.1 |
| Cys | 0 |
| Val | 4.6 |
| Met | 0 |
| Ile | 1.3 |
| Leu | 3.9 |
| Tyr | 5.1 |
| Phe | 5.7 |
| Lys | 6.8 |
| His | 3.1 |
| Arg | 9.3 |
| Trp | 0; | said polypeptide being isolated in a process comprising the sequential steps of:
a) a first ion-exchange chromatography on carboxymethyl cellulose, wherein said polypeptide is eluted in 250 mM sodium chloride in 10 mM phosphate buffer, pH 6.0;
b) a gel filtration chromatography on Sephadex G-50;
c) a second ion-exchange chromatography on carboxymethyl cellulose, wherein said polypeptide is eluted with a linear gradient of 25-100 mM sodium chloride in phosphate buffer, pH 6.0;
d) a third ion-exchange chromatography on carboxymethyl Sepharose, wherein said polypeptide is eluted stepwise in 260 mM sodium chloride in 10 mM phosphate buffer, pH 6.0;
e) a fourth ion-exchange chromatography on carboxymethyl Sepharose column, wherein said polypeptide is eluted with linear gradient of 0.1-0.5M ammonium formate; and
f) a reverse-phase high performance liquid chromatography, wherein said polypeptide is eluted with a linear gradient of 15% of 0.05% trifluoroacetate/99% acetonitrile in 0.05% trifluoroacetate/water and 50% of 0.05% trifluoroacetate/99% acetonitrile in 0.05% trifluoroacetate/water.

* * * * *